(12) United States Patent
Ghanam et al.

(10) Patent No.: US 11,980,425 B2
(45) Date of Patent: May 14, 2024

(54) TRACKER FOR A SURGICAL NAVIGATION SYSTEM

(71) Applicant: Stryker European Operations Holdings LLC, Kalamazoo, MI (US)

(72) Inventors: Fadi Ghanam, Schallstadt (DE); Jochen Breisacher, Teningen (DE); Florian Herrmann, Schwanau (DE); Emeric Umbdenstock, Freiburg (DE); Reinhold Zimmermann, Freiburg (DE); Gerd Ulrich Gamm, Freiburg (DE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 598 days.

(21) Appl. No.: 16/388,354

(22) Filed: Apr. 18, 2019

(65) Prior Publication Data

US 2019/0321108 A1    Oct. 24, 2019

(30) Foreign Application Priority Data

Apr. 19, 2018 (EP) ..................... 18168182

(51) Int. Cl.
*A61B 34/20* (2016.01)
*A61B 10/02* (2006.01)

(52) U.S. Cl.
CPC .......... *A61B 34/20* (2016.02); *A61B 10/0233* (2013.01); *A61B 2034/2055* (2016.02); *A61B 2034/2057* (2016.02); *A61B 2034/2072* (2016.02)

(58) Field of Classification Search
CPC . A61B 34/20; A61B 34/30; A61B 2034/2055; A61B 2034/2057; A61B 2034/2072; A61B 10/0233
See application file for complete search history.

(56) References Cited

U.S. PATENT DOCUMENTS

2003/0093103 A1    5/2003    Malackowski et al.
2003/0187351 A1*  10/2003    Franck ................... A61B 90/10
                                                          600/429

(Continued)

FOREIGN PATENT DOCUMENTS

DE    102013014524 A1    3/2015
EP         2263529 A1    12/2010

(Continued)

OTHER PUBLICATIONS

Jason; Using diodes to limit current to LEDs; published online on Nov. 26, 2009; Electrical Engineering; https://electronics.stackexchange.com/questions/263/using-diodes-to-limit-current-to-leds (Year: 2009).*

(Continued)

*Primary Examiner* — Chao Sheng
(74) *Attorney, Agent, or Firm* — Howard & Howard Attorneys PLLC (57) ABSTRACT

A tracker for a surgical navigation system, a tracker system, and a surgical navigation system are provided. The tracker comprises a carrier and an electrical circuit disposed on the carrier. The electrical circuit comprises at least one infrared light emitting diode, IR-LED, and a battery or a wireless power reception device configured to receive power wirelessly, wherein the battery or the wireless power reception device is configured to provide power to operate the at least one IR-LED. The electrical circuit is configured to limit a current for at least one of the at least one IR-LED to not exceed 15 mA.

20 Claims, 8 Drawing Sheets

(56) References Cited

U.S. PATENT DOCUMENTS

| | | | |
|---|---|---|---|
| 2004/0263494 A1* | 12/2004 | Poor | G06F 1/1656 |
| | | | 345/204 |
| 2005/0168168 A1* | 8/2005 | Elliott | H05B 31/50 |
| | | | 315/247 |
| 2007/0081695 A1* | 4/2007 | Foxlin | G06T 7/73 |
| | | | 382/103 |
| 2008/0312530 A1* | 12/2008 | Malackowski | A61B 5/06 |
| | | | 600/426 |
| 2009/0196033 A1 | 8/2009 | Macdonald | |
| 2013/0342704 A1 | 12/2013 | Williams et al. | |
| 2016/0007849 A1 | 1/2016 | Krueger | |
| 2017/0007334 A1 | 1/2017 | Crawford et al. | |
| 2017/0094197 A1* | 3/2017 | Beall | G06F 3/005 |
| 2017/0258535 A1 | 9/2017 | Crawford et al. | |
| 2018/0325621 A1* | 11/2018 | Srimohanarajah | A61B 90/39 |

FOREIGN PATENT DOCUMENTS

| | | | | |
|---|---|---|---|---|
| WO | WO-2010106524 A2 * | 9/2010 | | A46B 15/0044 |
| WO | 2015144246 A1 | 10/2015 | | |
| WO | 2018032084 A1 | 2/2018 | | |

OTHER PUBLICATIONS

Passerby; Resistor for 20 LEDs in series; published online on Apr. 15, 2016; Electrical Engineering; https://electronics.stackexchange.com/questions/228500/resistor-for-20-leds-in-series (Year: 2016).*

Hans; 3 RGB-LED with only 3 resistors; published online on Mar. 25, 2012; Electrical Engineering; https://electronics.stackexchange.com/questions/28699/3-rgb-led-with-only-3-resistors (Year: 2012).*

Button Cell—Wikipedia; https://en.wikipedia.org/wiki/Button_cell (Year: 2022).*

Partial Machine-Assisted English Language Translation for Grotz, Bernhard, "Grundwissen Elektronik", Release 0.1.6e, pp. 69-71, 120, dated Sep. 23, 2017, generated from Google Translate on May 13, 2019, 5 pages.

Grotz, Bernhard, "Grundwissen Elektronik", Release 0.1.6e, pp. 69-71, 120, dated Sep. 23, 2017, pp. 1-142.

Machine-assisted English language abstract and machine-assisted English translation for DE 10 2013 014 524 extracted from espacenet.com database on Nov. 25, 2019, 11 pages.

Horowitz, Paul et al., "The Art of Electronics", Cambridge University Press, 3rd Edition, 2015, p. 583.

Machine-assisted English translation of portions of and original document of Burklin Electronics, "Infrared LEDs", www.buerklin.com/de/Halbleiter/Optoelektronische-Bauelemente/Infrarot_LEDs/c/10141800? GRID_OR_LIST . . . , 2022, 7 pages.

Machine-assisted English translation of portons of and original document of Conrad, "IR LED, IR Diode, IR Emitter", https://www.conrad.de/de/ir-led-ir-emitter-0212521.html, 2022, 23 pages.

Kisomi, Alireza Avakh et al., "A Novel Wireless Ring-Shaped Multi-Site Pulse Oximeter", IEEE Symposium on Circuits and Systems, May 22, 2016, pp. 2451-2454.

Machine-assisted English translation of portions of and original document of MERCATEO, "Buy IR Emitters Cheaply from Mercateo", https://www.mercateo.com/kw/ir(20)emitter/ir)emitter.html . . . . , 2022, 7 pages.

* cited by examiner

TRACKER FOR A SURGICAL NAVIGATION SYSTEM

RELATED APPLICATIONS

This application claims priority to European Patent Application No. 18 168 182.6, filed 19 Apr. 2018, the content of which is incorporated herein by reference in its entirety.

TECHNICAL FIELD

The present disclosure generally relates to a tracker for use in surgical navigation. In particular, a tracker comprising an infrared light emitting diode is presented.

BACKGROUND

During surgery, a surgeon often uses instruments that have to be inserted into the body of a patient. Once inside the patient's body, the surgeon loses vision of the tip of the instrument. In order to help the surgeon navigate the instrument in such a case, a surgical navigation system can be used that tracks the instrument and provides visual or acoustic guidance to the surgeon.

One way to track the instrument is to attach a tracker onto the instrument. A camera in the operating room detects the tracker and generates data that is used to calculate the position of the tracker and, therefore, of the instrument. Commonly, the patient is tracked also, which enables calculating the position of the instrument relative to the patient.

Surgical navigation can be carried out using passive or active trackers. A passive tracker comprises markers that reflect light. The reflected light can be detected by the camera. However, passive markers are susceptible to contamination (e.g., with blood), which impairs their reflectivity and consequently the accuracy of the surgical navigation.

An active tracker, on the other hand, generates light (e.g., via a light emitting diode) that can be detected by the camera. Therefore, a higher brightness can be achieved and light generation is not dependent on ambient lightning. However, light generation requires a power source for the tracker, usually in the form of a battery pack or a power cord. The weight of the battery pack or of the power cord greatly affects the centre of gravity of the instrument. This can make holding the instrument tiresome for the surgeon. Furthermore, structurally weak instruments like biopsy needles may deform or even be damaged by the weight of the tracker.

The power consumption of the tracker may be reduced by operating the light emitting diodes in a pulsed manner. However, such a pulsed operation requires synchronization with the navigation camera, which leads to additional processing steps and increases the complexity of the tracker in view of the required communication interface.

SUMMARY

There is a need for a tracker that solves one or more of the aforementioned problems.

According to one aspect, a tracker for a surgical navigation system is provided. The tracker comprises a carrier and an electrical circuit disposed on the carrier. The electrical circuit comprises at least one infrared light emitting diode, IR-LED. The electrical circuit further comprises a battery or a wireless power reception device configured to receive power wirelessly, wherein the battery or the wireless power reception device is configured to provide power to operate the at least one IR-LED. The electrical circuit is configured to limit a current for at least one of the at least one IR-LED to not exceed 15 milliampere (mA).

The tracker is in particular a surgical navigation tracker. The tracker may be configured to be used in surgical navigation.

The tracker may comprise one, two, three, four or more IR-LEDs. In the case that the tracker comprises more than two IR-LEDs, the tracker may comprise an arrangement of the more than two IR-LEDs that is asymmetrical, e.g., that has no mirror symmetry or rotational symmetry. The tracker may comprise an arrangement of the more than two IR-LEDs such that each distance between any two IR-LEDs is unique. The carrier may be manufactured from a lightweight non-metallic material, such as a polymer.

The electrical circuit may comprise a printed circuit board. The electrical circuit may comprise at least one switch configured to electrically open and/or close at least a portion of the electrical circuit (e.g., to jointly switch the IR-LEDs on or off). The tracker may be a disposable item. In such a case, the switch may be operable exactly once to close the at least one portion of the electrical circuit. Such a switch may comprise an isolating material, such as paper and/or plastic. The isolating material may be physically removable from the tracker.

Operation of the IR-LED may comprise illumination of the IR-LED. The electrical circuit may be configured to limit the current for at least one of the at least one IR-LED to not exceed 10 mA, preferably 5 mA, more preferably 3 mA. The electrical circuit may be configured to limit a maximum current or average current for at least one of the at least one IR-LED to be in a range between 0.01 mA and 10 mA, for example between 0.05 mA and 5 mA or between 0.1 mA and 3 mA. The electrical circuit may be configured to limit the current for some or all of a plurality of IR-LEDs of the tracker to 15 mA or less as indicated above.

The tracker may be configured for continuous operation of at least one of the at least one IR-LED. The tracker may be configured for continuous operation of some or all of a plurality of IR-LEDs. The tracker may be configured for quasi-continuous operation of at least one of the at least one IR-LED. The quasi-continuous operation may be performed at an operation frequency of over 0.5 kilohertz (kHz), over 1 kHz or over 4 kHz. Since a continuous or quasi-continuous operation requires no synchronization with a camera, no communication interface (such as a transceiver) for communication with the camera is necessary. The tracker may thus not comprise a communication interface.

The electrical circuit may comprise at least one resistor configured to limit the current for the at least one of the at least one IR-LED. The at least one resistor may be electrically connected to a printed circuit board. The at least one resistor may be encased by the carrier. Each of the at least one IR-LED may be electrically connected in series to a respective resistor. Alternatively, at least a subset of the at least one IR-LED may be connected in parallel and consequently connected in series to a single resistor. The electrical circuit may comprise at least one voltage regulator circuit configured to limit the current for the at least one of the at least one IR-LED. The at least one voltage regulator circuit may comprise the at least one resistor.

The current for the at least one of the at least one IR-LED may be limited by an internal electrical resistance of the at least one of the at least one IR-LED and an electrical resistance of the at least one resistor electrically connected in series to the at least one of the at least one IR-LED. The current for the at least one of the at least one IR-LED may be limited by more than one resistor electrically connected in series to the at least one of the at least one IR-LED.

The electrical circuit may be configured to limit a radiant intensity of at least one of the at least one IR-LED to not exceed 40 microwatts per steradian (μW/sr), preferably 20 μW/sr, more preferably 10 μW/sr. The electrical circuit may be configured to limit a maximum radiant intensity or average radiant intensity of at least one of the at least one IR-LED to be in a range between 0.1 μW/sr and 40 μW/sr, for example between 0.5 μW/sr and 20 μW/sr or between 1 μW/sr and 10 μW/sr. The electrical circuit may be configured to limit a radiant intensity of some or all of a plurality of IR-LEDs to 40 μW/sr or less as indicated above.

The battery may be a button cell (also called a coin cell). The battery may comprise a plurality of cells. The battery may comprise zinc or lithium. The battery may be a zinc-air battery. The battery may be a CR2032 or CR2025 type battery. The battery may have a capacity of between 100 milliamp hours (mAh) and 1000 mAh (e.g., between 200 mAh and 400 mAh). The battery may be a primary battery that is not rechargeable. Alternatively, the battery may be a secondary battery that is rechargeable. The battery may be removable from the tracker by a user. Alternatively, the battery may not be removable from the tracker by a user (e.g., when the tracker is configured as a disposable item). Due to the limited current for at least one of the at least one IR-LED, the battery or the wireless power reception device may be sufficient as a power source and no external power source may be required. The tracker may not comprise a power cord to an external power source. The wireless power reception device may be configured for receiving power through at least one near field technique such as inductive coupling, capacitive coupling and magnetodynamic coupling.

The tracker may comprise a plurality of IR-LEDs, wherein a distance between at least two of the plurality of IR-LEDs may be smaller than 40 millimeters (mm), preferably 35 mm, more preferably 30 mm. A distance between at least two of the plurality of IR-LEDs may be in a range between 1 mm and 40 mm, for example between 3 mm and 35 mm or between 5 mm and 30 mm. The IR-LEDs may be disposed in a common plane. Alternatively, the IR-LEDs may not be disposed in a common plane.

The tracker may further comprise an interface that is configured for coupling the tracker to a surgical instrument or to a patient. The interface may comprise at least one of a fixation screw, an opening, a clamp, an attachment screw, a snap lock, a magnet and a ferromagnetic material. The interface may comprise an adhesive, e.g., in form of an adhesive tape. The interface may be configured to couple the tracker to a shaft portion (e.g., a shaft with a cylindrical form) or an end portion of the surgical instrument. The surgical instrument may be a biopsy needle, a drill, a saw, a pointer, a cutter or a measurement device. The surgical instrument may be an instrument configured for use in surgeries related to ear, nose and throat (ENT). The surgical instrument may be an instrument configured for use in neurosurgery (e.g., cranial surgery).

A tracker system for a surgical navigation may comprise the tracker and a surgical instrument. The tracker may be attached or attachable to the surgical instrument.

The tracker may comprise a plurality of IR-LEDs and be configured to operate at least two of the plurality of the IR-LEDs simultaneously. The tracker may be configured to operate all IR-LEDs simultaneously. Alternatively, the tracker may be configured to operate the plurality of the IR-LEDs sequentially.

The weight of the tracker may not exceed 35 grams (g), preferably 25 g, more preferably 15 g. The weight of the tracker may be in a range between 1 g and 35 g, for example between 3 g and 25 g or between 5 g and 15 g.

According to a second aspect, a surgical navigation system is presented. The surgical navigation system comprises a tracker as presented herein and a camera capable of detecting light of the at least one IR-LED and of generating a camera signal indicative of the detected light.

The surgical navigation system may further comprise a processor capable of receiving the camera signal and at least one of registering and tracking the tracker based on the received sensor signal. The processor may be configured to generate a visual or acoustic signal indicative of the tracking. The tracker may comprise a plurality of IR-LEDs, wherein the IR-LEDs have a spatial relation to each other, and wherein the processor has access to information about the spatial relation.

The camera may comprise at least one two-dimensional image sensor. The at least one two-dimensional image sensor may enable tracking of a plurality of simultaneously illuminated IR-LEDs. A single two-dimensional image sensor may enable tracking a plurality of IR-LEDs, wherein the surgical navigation system (e.g., a processor thereof) has access to information about a spatial relation between a plurality of IR-LEDs. Alternatively, two or more two-dimensional image sensors of the camera may enable tracking a plurality of IR-LEDs, wherein the two or more two-dimensional image sensors are configured to be operated in a stereo mode.

The camera may comprise at least one lens for focusing the infrared light emitted by the at least one IR-LED. The camera may comprise a plurality of lenses for focusing the infrared light emitted by the at least one IR-LED. The camera may comprise at least one lens for each two-dimensional image sensor. The lens may increase the amount of light impinging on the two-dimensional image sensor. The camera may not comprise a slit aperture.

According to a third aspect, a method of operating a tracker is presented. The tracker comprises a carrier and an electrical circuit disposed on the carrier. The electrical circuit comprises at least one infrared light emitting diode, IR-LED, and a battery or a wireless power reception device configured to receive power wirelessly. The method comprises the step of providing, by the battery or the wireless power reception device, power to operate the at least one IR-LED. The method further comprises the step of limiting, by the electrical circuit, a current for at least one of the at least one IR-LED to not exceed 15 mA.

The method may further comprise detecting the light emitted by the at least one of the at least one IR-LED. The method may further comprise tracking the tracker based on the detected light.

BRIEF DESCRIPTION OF THE DRAWINGS

Further details, advantages and aspects of the present disclosure will become apparent from the following embodiments taken in conjunction with the drawings, wherein.

DETAILED DESCRIPTION

In the following description, exemplary embodiments of a tracker for surgical navigation, a surgical navigation system and a method for operating a tracker will be explained with reference to the drawings. The same or similar reference numerals will be used to denote the same or similar structural features.

Figure 1A:
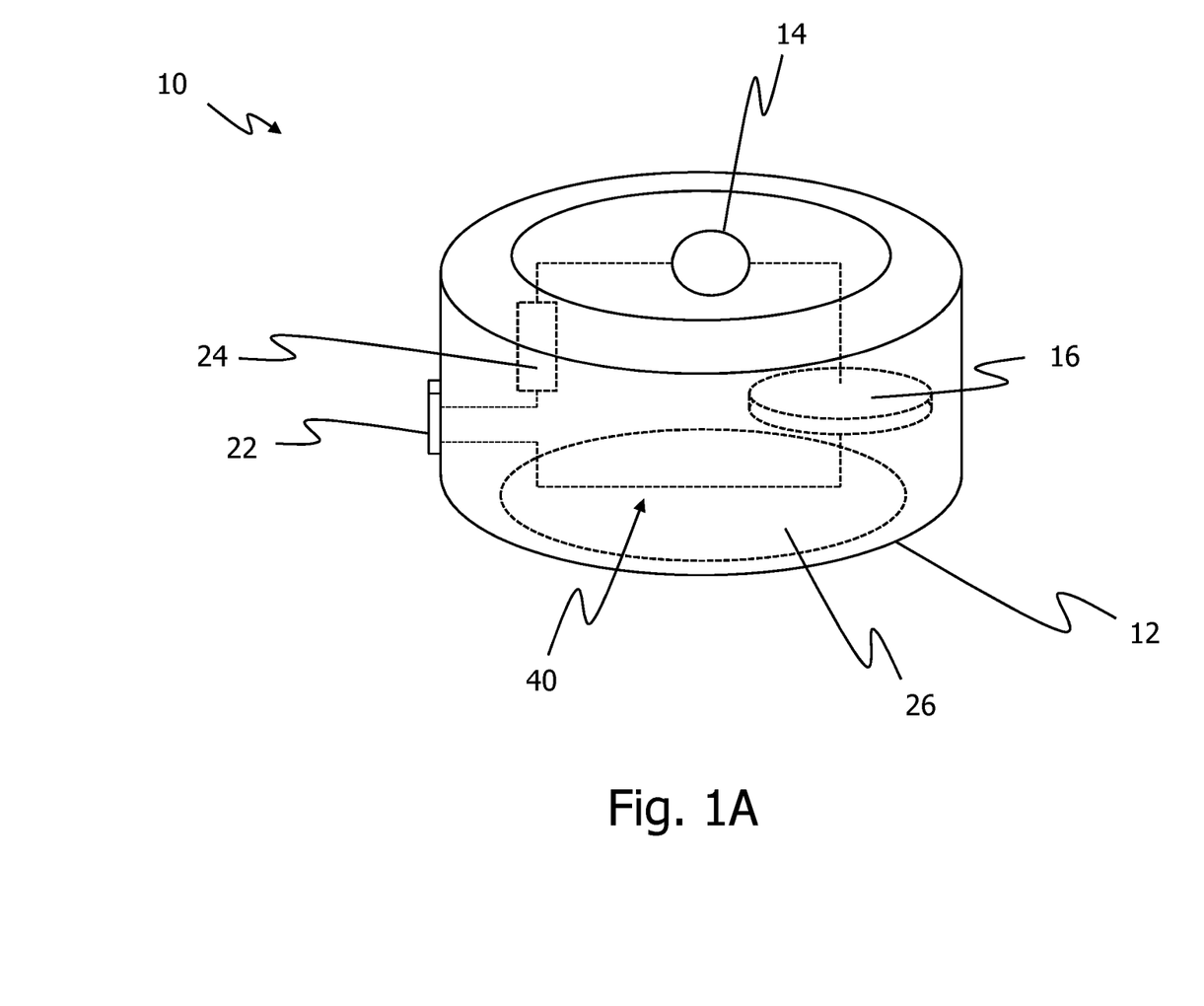
FIG. 1A shows a perspective view of a first embodiment of a tracker.

FIG. 1A shows a perspective view of a first embodiment of a tracker 10. The tracker 10 comprises a carrier 12 and an electrical circuit 40. Dashed lines indicate that elements of the tracker 10 are not visible in the perspective view (e.g., are located inside the tracker 10). The electrical circuit 40 comprises one infrared light emitting diode, IR-LED 14, a battery 16 and a resistor 24. The IR-LED 14, the battery 16 and the resistor 24 are electrically connected in series. Therefore, an electrical resistance of the resistor 24 limits the current for the IR-LED 14. The resistor 24 has an electrical resistance so that the current for the IR-LED 14 does not exceed 15 mA.

The electrical circuit 40 further comprises a switch 22 that is operable from the outside and configured to electrically open and close the electrical circuit 40. Therefore, the IR-LED 14 may be operated by operating the switch 22, which opens and closes the electrical circuit 40 that connects the battery 16 with the IR-LED 14. Alternatively, the switch 22 may be configured to only close the electrical circuit 40. Such a one-time use may be realized by the switch 22 comprising a removable isolating material (e.g., a paper strip), wherein the switch 22 is configured to close the electrical circuit 40 upon removal of the isolating material.

The IR-LED 14 emits infrared light which can be sensed by a surgical navigation system. Since ambient lighting for the surgeon emits in the visible light spectrum, the brightness of the IR-LED 14 detectable by the surgical navigation system is essentially independent from the brightness of the ambient lighting. Therefore, due to the IR-LED 14 emitting infrared light, the IR-LED 14 may be operated with a low brightness caused by a low current that is limited to not exceed 15 mA.

The tracker 10 is configured for continuous operation of the IR-LED 14. Alternatively, the tracker may be configured for quasi-continuous operation. The quasi-continuous operation may be performed at an operation frequency of over 0.5 kHz. Such a quasi-continuous operation reduces the power consumption of the tracker 10.

The tracker 10 further comprises an interface 24 for coupling the tracker 10 to a patient. In this example, the interface 24 comprises an adhesive that is configured to attach the tracker 10 onto a body surface of the patient, such as skin. A single tracker 10 or a plurality of trackers 10 as shown in FIG. 1A may be attached to the patient for being tracked by the surgical navigation system.

Figure 1B:
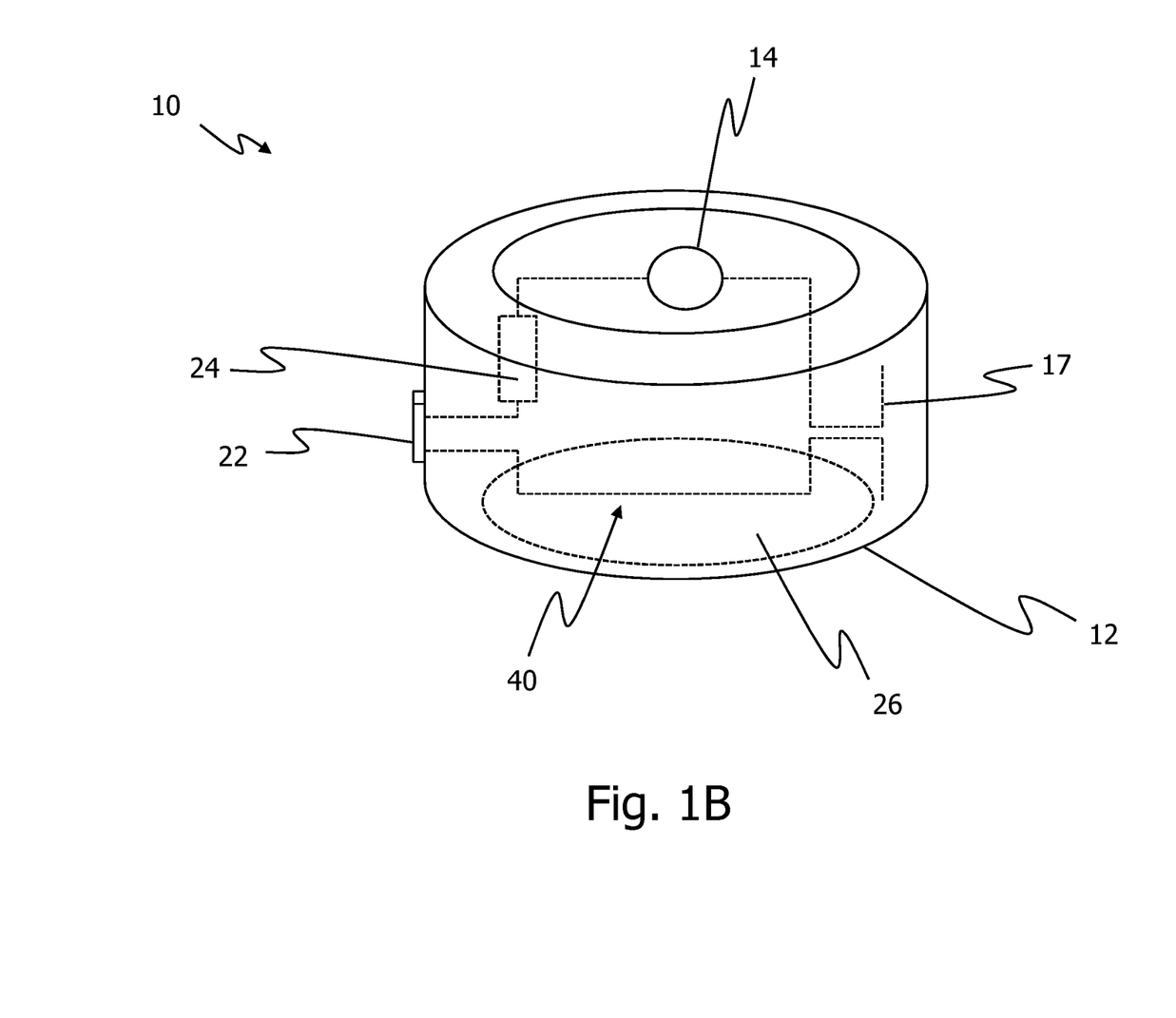
FIG. 1B shows a perspective view of a second embodiment of a tracker.

FIG. 1B shows a perspective view of a second embodiment of a tracker 10. The tracker shown in FIG. 1B differs from the tracker shown in FIG. 1A essentially in that the tracker 10 comprises a wireless power reception device 17 instead of a battery (cf. reference sign 16 in FIG. 1A). The wireless power reception device 17 comprises a dipole antenna configured for receiving power in form of electromagnetic waves. The wireless power reception device 17 may additionally or alternatively comprise a coil for coupling to an electro-magnetic field. For inductive coupling, reference is made to document US Publication No. 2003/0093103 A1.

Figure 2:
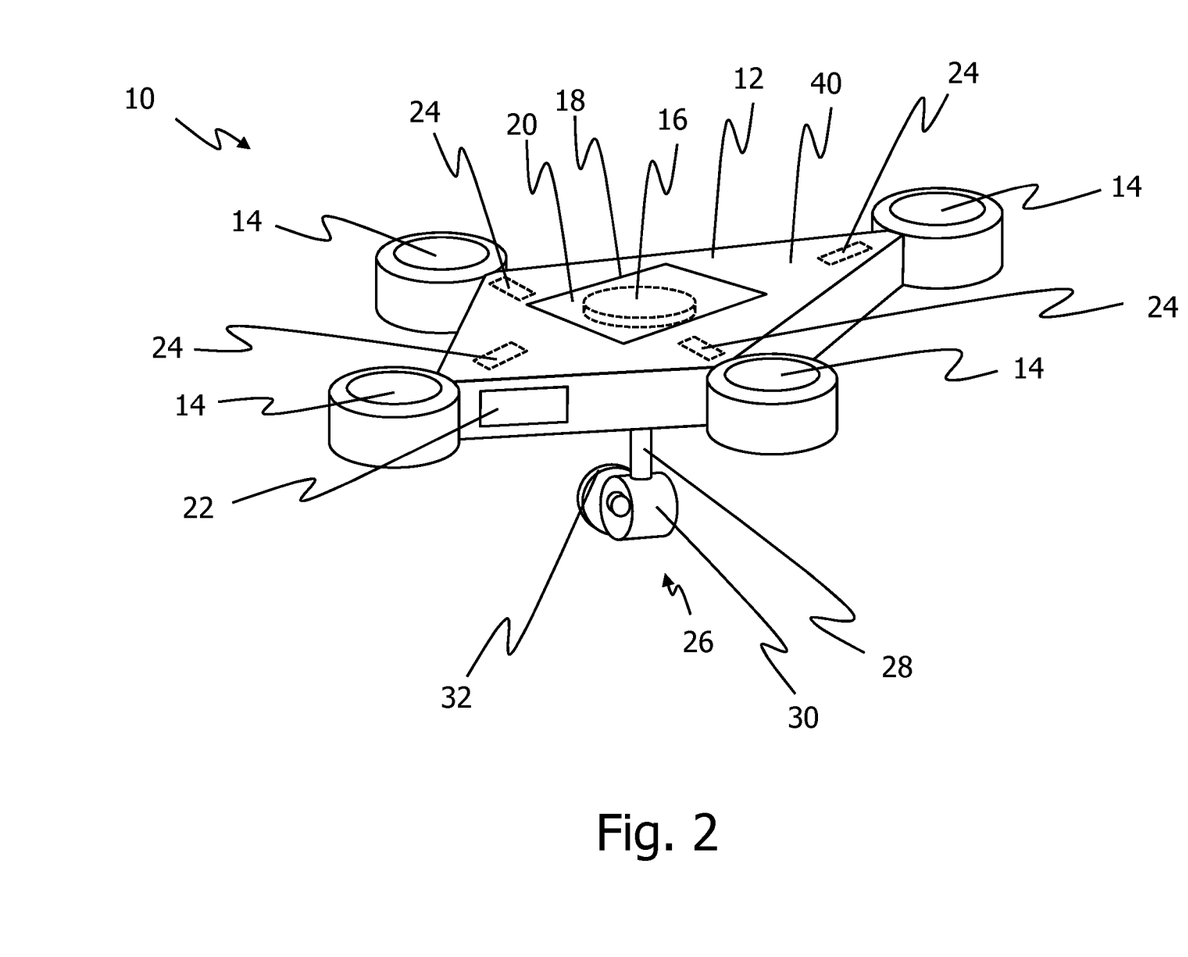
FIG. 2 shows a perspective view of a third embodiment of a tracker.

FIG. 2 shows a perspective view of a third embodiment of a tracker 10. The tracker 10 comprises a carrier 12 and an electrical circuit 40, wherein electric wiring of the electrical circuit 40 is not displayed in FIG. 2 for the sake of clarity. The electric wiring of the electrical circuit 40 is discussed further below in combination with FIGS. 6A-C.

The electrical circuit 40 comprises a plurality of infrared light emitting diodes, IR-LEDs, 14 that are mechanically connected to the carrier 12. The tracker 10 illustrated in FIG. 2 comprises exactly four IR-LEDs 14. For example, the tracker 10 comprises three IR-LEDs 14 for three dimensional tracking as well as a fourth IR-LED 14 for redundancy. Alternatively, the tracker 10 may comprise a different number of IR-LEDs 14. The tracker 10 may comprise three IR-LEDs 14, which reduces the power consumption of the tracker 10. The tracker 10 may comprise two IR-LEDs 14 for tracking movement with limited degrees of freedom (such as five degrees of freedom) of, for example, a surgical instrument. The tracker 10 may comprise five or more IR-LEDs 14 for an increased redundancy.

The electrical circuit 40 further comprises a battery 16. The battery 16 is realized as a single coin cell. The battery 16 may also comprise a plurality of coin cells. Coin cells are batteries with little weight resulting in a tracker 10 with a reduced weight. The battery 16 may be a primary battery for a one-time use or secondary battery that is rechargeable. The battery may be a CR2032 type battery. The battery 16 is displayed with dashed lines to indicate that the battery 16 is disposed in a compartment 18 inside the tracker 10, wherein a lid 20 is configured to close the compartment 18. The lid 20 protects the battery 16 from contaminants that may occur during surgery (e.g., blood, water and sterilization agents).

The electrical circuit 40 comprises electrical wiring (not shown in FIG. 2) that electrically connects the battery 16 to each of the IR-LEDs 14. The IR-LEDs 14 are electrically connected in parallel with each other. Therefore, if one of the IR-LEDs 14 fails, the electrical connection of the battery 16 with the remaining IR-LEDs 14 is not interrupted. The tracker 10 further comprises a switch 22 that is configured to open and close an electrical connection between the battery 16 and the IR-LEDs 14. Alternatively, a plurality of switches may be provided configured to individually control power supply to each IR-LED 14. As a further alternative, the tracker 10 may comprise at least one one-time use switch. Such a one-time use may be realized by the switch 22 comprising a removable isolating material (e.g., a paper or plastic strip), wherein the switch 22 is configured to close the electrical circuit 40 upon removal of the isolating material.

The electrical circuit 40 further comprises resistors 24. In the embodiment of FIG. 2, the tracker 10 comprises four resistors 24, equal to the number of IR-LEDs 14. The tracker 10 may alternatively comprise a different number of resistors 24 (see FIGS. 5A-C). Each resistor 24 is disposed between the battery 16 and its corresponding IR-LED 14.

The resistors 24 are displayed in dashed lines to indicate that they are disposed inside the carrier 12. Each resistor 24 is electrically connected in series to its corresponding IR-LED 14. Therefore, a resistor 24 may be connected between its corresponding IR-LED 14 and a positive or a negative terminal of the battery 16.

The tracker 10 further comprises a mechanical interface 26 for coupling the tracker 10 to a surgical instrument (not shown). The interface 26 comprises an extension in form of a bar 28 that spaces the tracker 10 apart from the surgical instrument. The bar 28 connects the tracker 10 to an attachment ring 30. The attachment ring 30 comprises a cylindrical opening configured to receive the surgical instrument. The interface 26 comprises a fixation screw 32 that extends through a threaded opening in a wall of the attachment ring 30. By turning the fixation screw 32, a radial extension of the fixation screw 32 into the cylindrical opening of the attachment ring 30 can be adjusted. Therefore, the fixation screw 32 can be adjusted to exert a radial force onto a surgical instrument received by the attachment ring 30. Once the fixation screw 32 is tightened to achieve a sufficient clamping force, the tracker 10 is securely attached to the surgical instrument, enabling the surgical instrument to be moved in synchronicity with the tracker 10 attached thereto.

Figure 3:
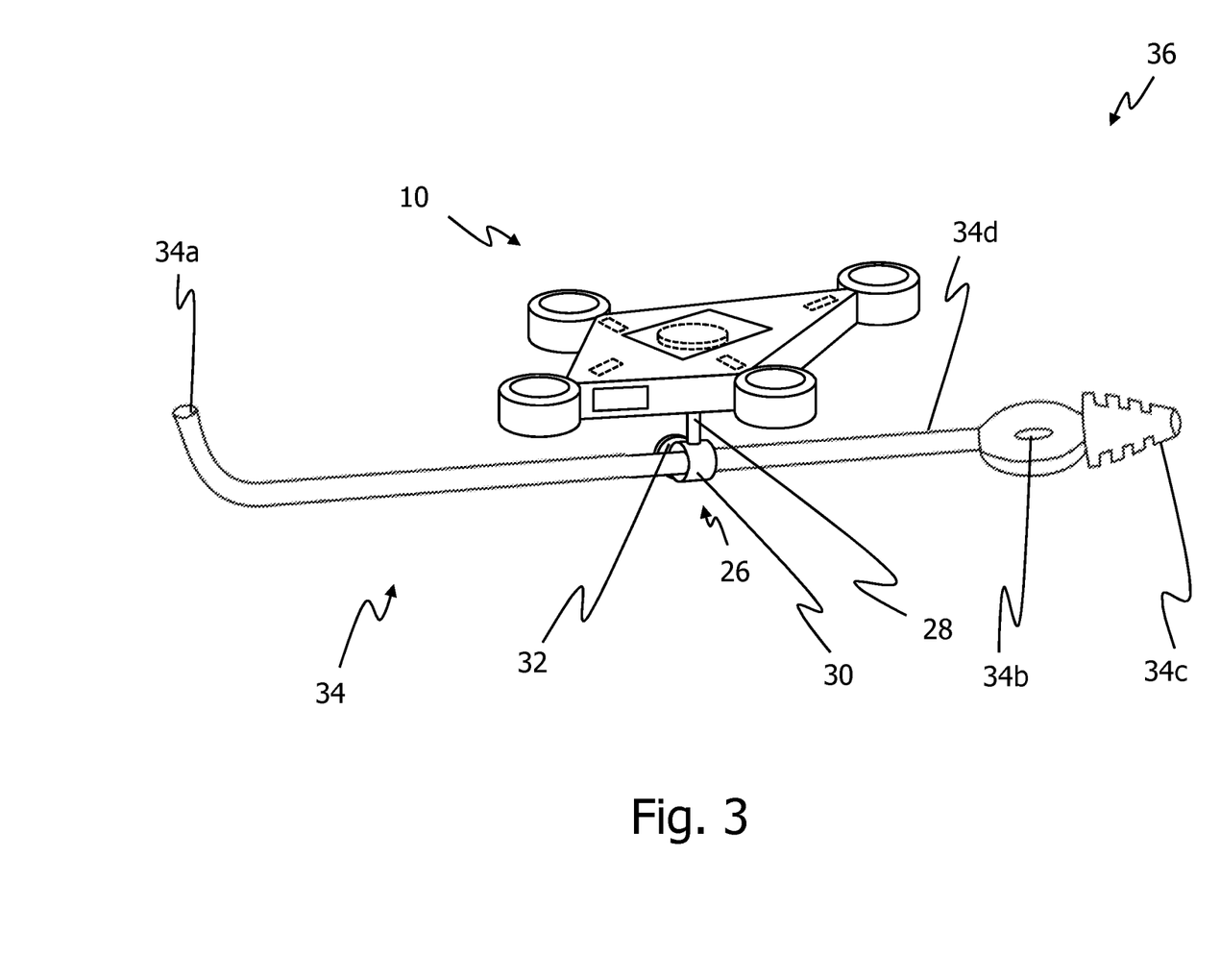
FIG. 3 shows a perspective view of the tracker embodiment of FIG. 2 attached to a surgical instrument.

FIG. 3 shows a perspective view of the tracker embodiment of FIG. 2 attached to a surgical instrument in form of a suction tube 34. The surgical instrument 34 and the tracker 10 are comprised by a tracker system 36, wherein the tracker 10 is attached to the surgical instrument 34. The surgical instrument 34 is not limited to the suction tube 34 shown in FIG. 3 and may be any other instrument used in surgery. The suction tube 34 comprises a suction tip 34a with an opening that receives liquids to be removed from a surgery site. The suction tube 34 further comprises a hole 34b for manually controlling the suction force of the suction tube 34 as well as a suction tube interface 34c for coupling the suction tube 34 to a suction line. The suction tube 34 further comprises a suction tube shaft 34d that leads removed liquids to the suction tube interface 34c.

The suction tube shaft 34d is usually structurally weak, particularly in the case of an elastic suction tube shaft 34d. A heavy tracker (e.g., with a weight of over 100 g) attached to the tube shaft 34d may bend the suction tube shaft 34d, which impairs operation of the surgical instrument 34 and affects accuracy of a tracking of the surgical instrument 34. A heavy tracker may also bend and/or damage other surgical instruments such as a biopsy needle or a surgical instrument used in ENT surgeries. Surgical instruments used in neurosurgery are also often thin and therefore prone to bending.

FIG. 3 shows a perspective view of the embodiment of the tracker of FIG. 2 attached to the suction tube 34. As described above, the suction tube 34 is received by the attachment ring 30. The fixation screw 32 is adjusted in such a way that the suction tube 34 is clamped between the fixation screw 32 and the inner wall of the opening of the attachment ring 30.

Alternatively, the interface 26 may comprise a different fixation mechanism. The interface 26 may, for example, comprise a clamp that circumferentially encompasses a portion of the surgical instrument 34. The interface 26 may comprise an attachment screw that is configured to be screwed into a threaded portion of the surgical instrument 34. Conversely, the interface 26 may comprise a threaded portion configured to receive an attachment screw of the surgical instrument 34. The interface 26 may comprise a magnet configured to be attached to a ferromagnetic portion of the surgical instrument 34. Conversely, the interface 26 may comprise a ferromagnetic portion that is configured to be attached to a magnet of the surgical instrument 34.

The interface 26 is configured for coupling the tracker 10 to a shaft portion of the surgical instrument 34. Alternatively, the interface 26 may be configured for coupling the tracker 10 to an end portion of the surgical instrument 34.

As shown in FIG. 3, the bar 28 of the interface 26 extends out of a bottom surface of the carrier 12. In other words, the bar 28 extends in a direction facing away from the IR-LEDs 14. Alternatively, the bar 28 may extend in various angles or extend from a side surface of the carrier 12. Different extension directions of the bar 28 allow for different orientations of the tracker 10 relative to the surgical instrument 34. Therefore, the tracker 10 may be oriented in such a way that the IR-LEDs 14 are facing a camera.

Figure 4:
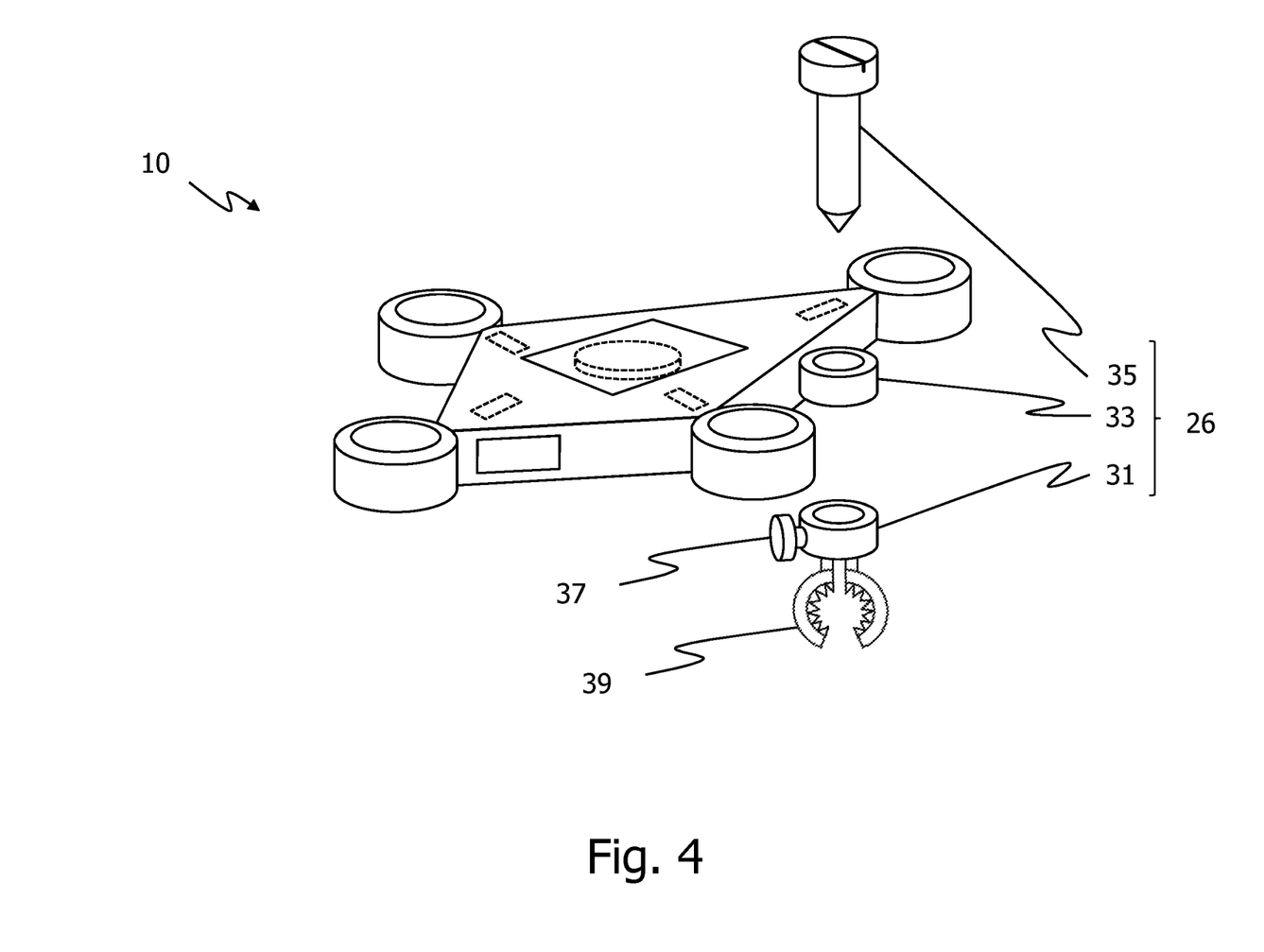
FIG. 4 shows a perspective view of a forth embodiment of a tracker.

FIG. 4 shows a perspective view of a third embodiment of a tracker 10. The tracker 10 shown in FIG. 2 and the tracker 10 shown in FIG. 4 essentially differ in the type of interface 26. FIG. 4 shows an interface 26 that comprises a clamp 31, wherein the clamp 31 comprises an adjustment screw 37 and clamping jaws 39. The adjustment screw 37 enables adjustment of a distance between the clamping jaws 39 and of a clamping force of the clamping jaws 39. The interface 26 further comprises an attachment opening 33 attached to the tracker 10 and a fastening screw 35, wherein the attachment opening 33 is configured to receive the fastening screw 35. The clamp 31 comprises a thread that is configured to receive the fastening screw 35. Therefore, the clamp 31 can be attached to the attachment opening 33 by tightening the fastening screw 35 extending through the attachment opening 33 against the thread of the clamp 31. The clamp 31 is configured to be attached to a surgical instrument (not shown) by positioning the surgical instrument between the clamping jaws 39 and adjusting the adjustment screw 37 until the clamping jaws 39 clamp the surgical instrument.

Alternatively, the tracker 10 and surgical instrument 34 may be mechanically connected for a one-time use. The tracker 10 and the surgical instrument 34 may be integrally formed (e.g., during injection molding). The tracker 10 may, for example, be integrally formed with a handle of the surgical instrument 34. With the tracker 10 already attached to the instrument 34, the surgeon can immediately use the surgical instrument 34 without having to attach the tracker 10 thereon. The surgeon may dispose of both the tracker 10 and the surgical instrument 34 after the one-time use.

The tracker 10 of FIGS. 3 and 4 may also be configured to be attached to a patient. Therefore, the interface 26 may alternatively comprise an adhesive surface.

Figure 5A:
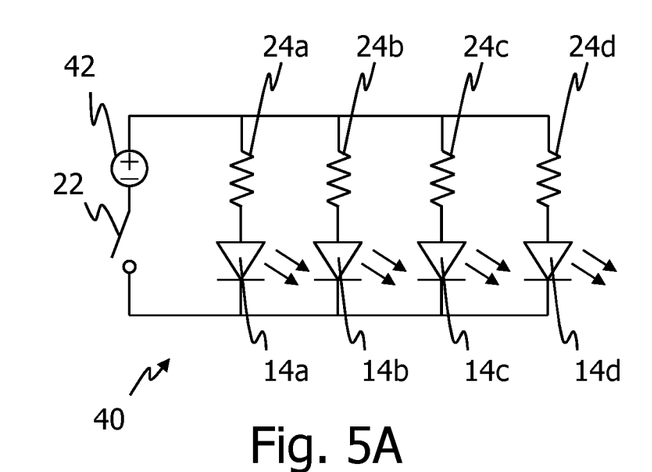
FIG. 5A shows a first embodiment of an electrical circuit employed in the tracker in FIG. 2.
Figure 5B:
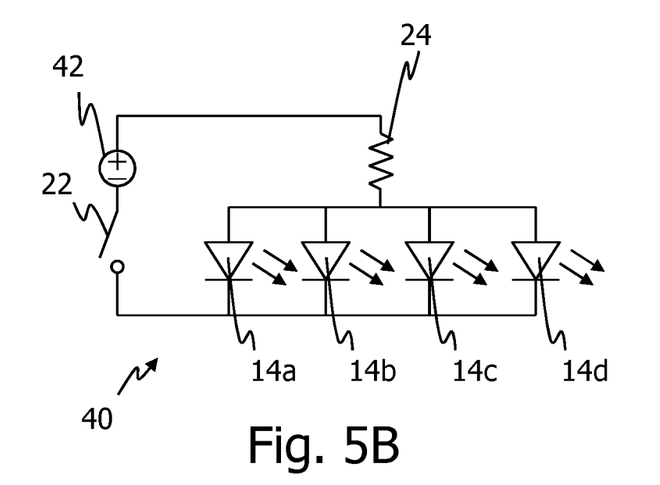
FIG. 5B shows a second embodiment of an electrical circuit employed in the tracker in FIG. 2.
Figure 5C:
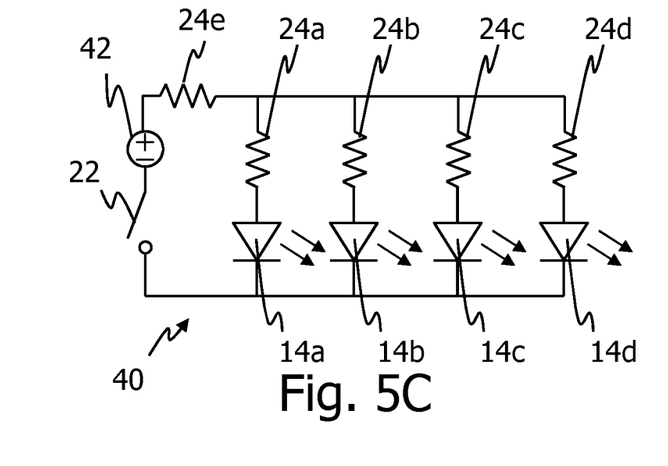
FIG. 5C shows a third embodiment of an electrical circuit employed in the tracker in FIG. 2.

FIGS. 5A-C show different embodiments of an electrical circuit 40 employed in the tracker 10 shown in FIG. 2.

FIG. 5A shows a first embodiment of the electrical circuit 40. The electrical circuit 40 comprises the battery 16. The electrical circuit 40 further comprises four IR-LEDs 14a, 14b, 14c, 14d which are all electrically connected in parallel to each other. The electrical circuit 40 also comprises the switch 22 that is configured to open and close the electrical connection between the battery 16 and the IR-LEDs 14. The electrical circuit 40 further comprises four resistors 24a, 24b, 24c, 24d, each of which being electrically connected in series to a corresponding IR-LED 14a, 14b, 14c, 14d. The resistors 24a, 24b, 24c, 24d are electrically connected between the IR-LEDs 14a, 14b, 14c, 14d and a positive terminal of the battery 16. Alternatively, at least one resistor 24 may be electrically connected between the corresponding IR-LEDs 14 and a negative terminal of the battery 16.

Each resistor 24a, 24b, 24c, 24d forms a series circuit with its corresponding IR-LED 14a, 14b, 14c, 14d. Furthermore, each IR-LED 14a, 14b, 14c, 14d contributes its own electrical resistance to the electrical resistance of the resulting series circuit. According to Ohm's law the current is inversely proportional to the resistance. Therefore, by adjusting the resistance of each resistor 24a, 24b, 24c, 24d a current through that resistor 24a, 24b, 24c, 24d as well as through its corresponding IR-LED 14a, 14b, 14c, 14d can be adjusted.

The battery 16 provides a direct current voltage of, for example, 3 V. Each of the IR-LEDs 14a, 14b, 14c, 14d has an operation voltage of, for example, 1.5 V. Therefore, 3V−1.5V=1.5V of the battery voltage drops off at each of the resistors 24a, 24b, 24c, 24d. The electrical resistance of each resistor 24a, 24b, 24c, 24d is 150Ω. Therefore, the current through each resistor 24a, 24b, 24c, 24d and consequently each IR-LED 14a, 14b, 14c, 14d is 1.5V/150Ω=10 mA. Due to the provision of the resistors 24a, 24b, 24c, 24d, the electrical circuit 40 is configured to limit a current for each of IR-LEDs 14a, 14b, 14c, 14d to not exceed 15 mA. In this way, the electrical circuit 40 also limits the radiant intensity of at least one of the IR-LEDs 14a, 14b, 14c, 14d to not exceed 40 µW/sr lumen.

The coin cell of the battery 16 has a low weight, but also a small capacity (e.g., 220 mAh). Since the electrical circuit 40 is configured to limit the current for each of the IR-LEDs to not exceed 15 mA, the capacity of a coin cell is still sufficient to safely operate the tracker 10 for the duration of a typical surgical navigation procedure. For example, with a C2032 type battery having a capacity of 220 mAh and providing power to four IR-LEDs 14 each with a current of 10 mA, the tracker 10 can be operated for a duration of 220 mAh/(4×10 mA)=5.5 h.

FIG. 5B shows a second embodiment of an electrical circuit 40 that may be employed in the tracker 10 of FIG. 2. A single resistor 24 is electrically connected in series to all IR-LEDs 14a, 14b, 14c, 14d. This embodiment comprises a lower amount of resistors and, therefore, has lower material costs. Alternatively, more than one resistor 24 may each be electrically connected in series to a plurality of the IR-LEDs 14a, 14b, 14c, 14d. For example, two resistors 24 may each be electrically connected in series to IR-LEDs 14a, 14b and 14c, 14d, respectively.

FIG. 5C shows a third embodiment of an electrical circuit 40 employed in the tracker 10 in FIG. 2. The third embodiment is essentially a combination of the first and second embodiments of the electrical circuit 40. Each one of the IR-LEDs 14a, 14b, 14c, 14d is electrically connected in series to a corresponding resistor 24a, 24b, 24c, 24d, forming a series circuit. All four series circuits are electrically connected in parallel and furthermore electrically connected in series to a further resistor 24e. This embodiment comprises more resistors 24, which allows for more possibilities to adjust currents in the electrical circuit 40. The electrical circuit 40 may comprise at least one voltage regulator circuit comprising the resistors 24.

Figure 6:
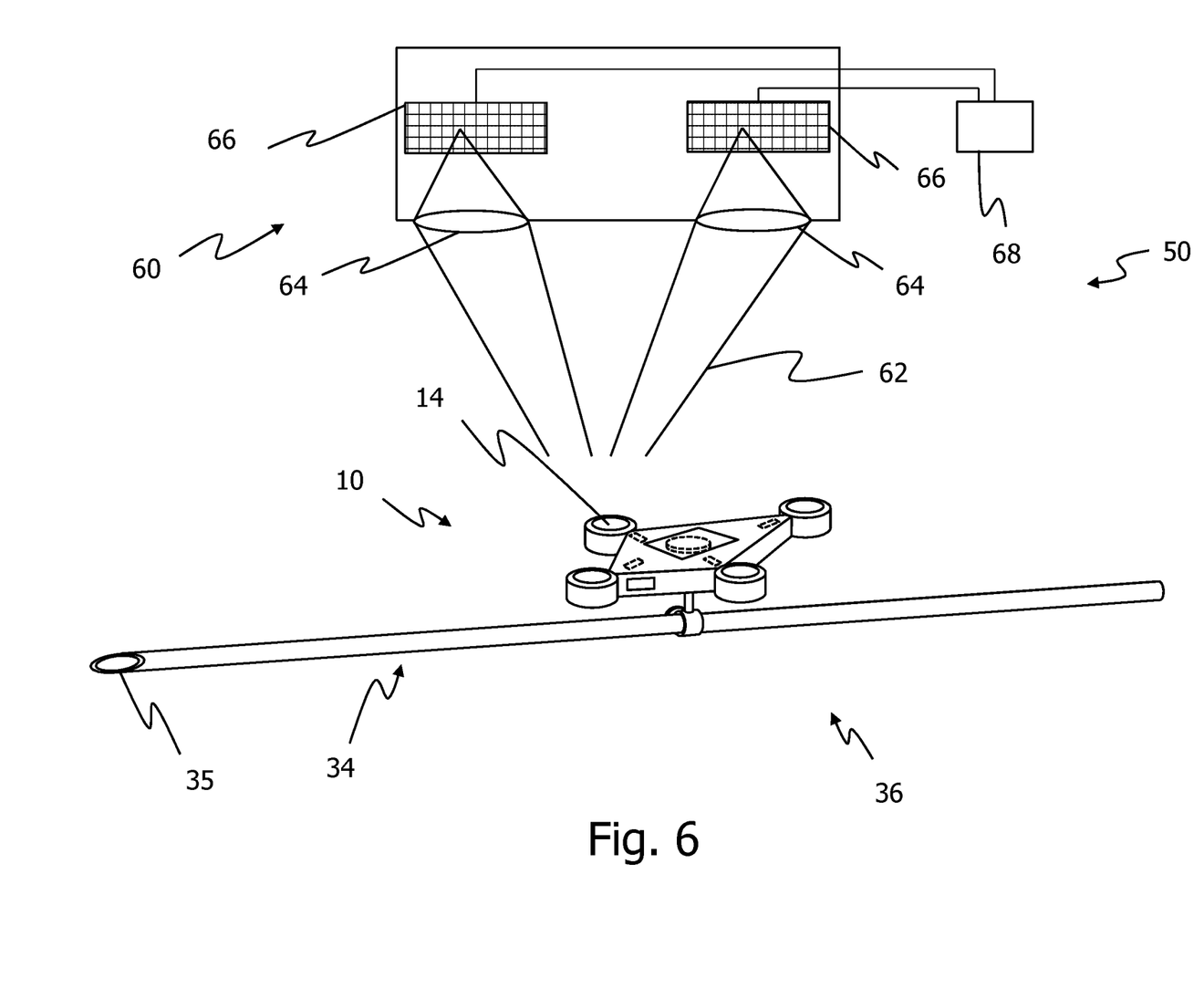
FIG. 6 shows a perspective view of an embodiment of a surgical navigation system.

FIG. 6 shows a perspective view of an embodiment of a surgical navigation system 50. The surgical navigation system 50 comprises the tracker 10 as described above and a camera 60. The camera 60 is capable of detecting light 62 of the plurality of IR-LEDs and of generating a camera signal indicative of the detected light 62. A tracker system 36 comprises the tracker 10 and a surgical instrument 34, wherein the tracker 10 is attached to the surgical instrument 34.

The camera 60 comprises two lenses 64 for focusing the infrared light emitted by the plurality of the IR-LEDs. The lenses 64 enable a larger amount of light to enter the camera 60 compared to a non-focusing opening like a slit aperture. Therefore, the camera is capable of detecting light sources with a low brightness, such as the IR-LEDs 14 being operated with limited currents.

The camera 60 further comprises two two-dimensional image sensors 66. The two-dimensional image sensors 66 are capable of sensing a solid angle (i.e., a two-dimensional angle). A conventional one-dimensional sensor row, on the other hand, typically requires synchronization with the detected light source and may only allow tracking of a single light source per scan. Since the two-dimensional image sensors 66 can detect all IR-LEDs 14 at once, the tracker 10 may be configured to operate at least two and in particular all of the plurality of the IR-LEDs 14 simultaneously. Such a simultaneous operation requires no synchronization of the camera 60 with the tracker 10. Therefore, the tracker 10 does not require a communication interface (e.g., a wireless transceiver) for communicating with the camera 60, which further reduces the weight of the tracker 10.

The surgical navigation system 50 comprises a processor 68 capable of receiving the camera signal. The processor 68 is capable of registering and tracking the tracker 10 based on the received sensor signal. Based on the camera signal, the processor 68 is also capable of calculating an orientation and distance of the tracker 10 relative to the camera 60. The processor 68 may further be configured to receive and/or store information of a patient's body (e.g., a computed tomography scan and/or tracking signal of the patient's body). The processor 68 may then calculate a position and orientation of the surgical instrument 34 relative to the patient's body. The processor 68 is configured to generate a visual or acoustic signal indicative of the tracking of the surgical instrument 34. The visual signal may be displayed on a screen. The processor 68 may be a part of a computing device separate from the camera 60. Alternatively, the camera 60 may comprise the processor 68.

The surgical navigation system shown in FIG. 6 comprises two two-dimensional image sensors 66 that are part of a stereo camera. Such a stereo camera is capable of capturing three-dimensional image data. Therefore, a known spatial relation between the IR-LEDs 14 is not necessary. A stereo camera may thus be employed when a plurality of single IR-LEDs 14 (such as shown in FIGS. 1A and 1B) are attached to a patient. Due to manual attachment, the spatial relation between the IR-LEDs is unknown. However, since the stereo camera is capable or capturing three-dimensional image data, the IR-LEDs 14 can be tracked by the stereo camera.

The surgical navigation system shown in FIG. 6 also shows a tracker with a fixed spatial relation between the IR-LEDs 14. The processor 68 may have access to information about the spatial relation. In such a case, three-dimensional images captured by a stereo camera would not be required and the camera 60 may only comprise a single two-dimensional image sensor 66.

The exemplary surgical instrument 34 shown in FIG. 6 is a biopsy needle 34. The tracker 10 is coupled to a shaft portion of the biopsy needle 34. Tracking the tracker 10 enables determining a position of a tip 35 of the biopsy needle 34 inside a patient's body (not shown). As explained above, the processor 68 is capable of calculating a position and orientation of the surgical instrument 34, and therefore also of the tip 35 of the biopsy needle 34 relative to the patient's body. Since the position of the tip 35 of the biopsy needle 34 can be determined, the tip 35 can be guided to a region of the patient's body previously located by a computed tomography scan. At that region tissue may be extracted using the biopsy needle 34.

Surgical instruments such as the biopsy needle 34 have little mass and may be structurally weak. When a heavy tracker (e.g., with a weight of 100 g or more) is attached to such a handheld surgical instrument 34, the tracker shifts the center of mass, which can be tiresome (e.g., due to a torque applied at the holding hand). Furthermore, the surgical instrument may deform (elastically or plastically) or even be damaged due to the weight of the attached heavy tracker. A bent biopsy needle reduces the accuracy of the tracking, as the tip 35 of the biopsy needle is offset compared to an unbent state of the biopsy needle 34. The tracker 10 illustrated in FIG. 6 typically has a reduced weight of 35 g or below. Therefore, the above mentioned disadvantages are reduced or eliminated. The biopsy needle 34 is less tiresome to hold by hand and is less deformed by the weight of the tracker 10.

Figure 7:
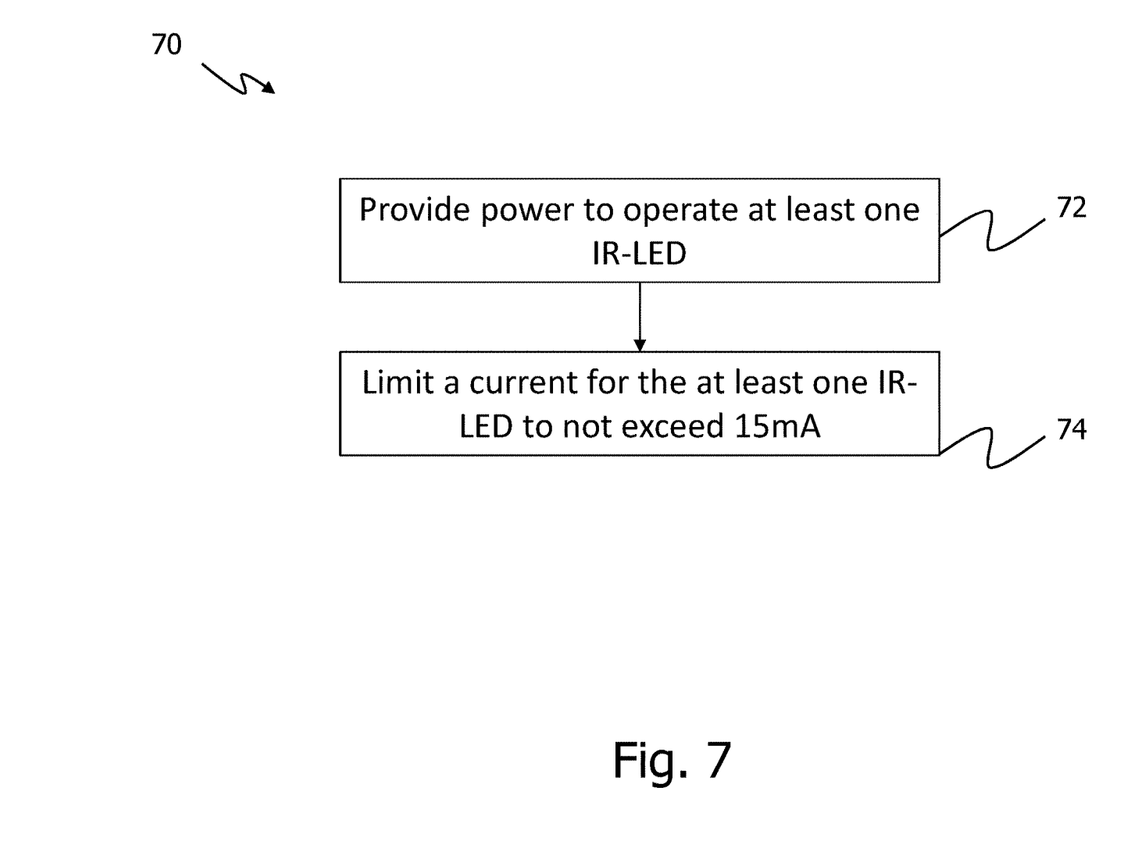
FIG. 7 shows a flow diagram of a method embodiment of operating a tracker.

FIG. 7 shows a flow diagram 70 of a method embodiment of operating a tracker. The tracker being operated may be the tracker 10 as shown in FIG. 1A, 1B or 2. The tracker comprises a carrier and an electrical circuit disposed on the carrier. The electrical circuit comprises at least one infrared light emitting diode, IR-LED, and a battery or a wireless power reception device configured to receive power wirelessly.

The method comprises providing in step 72, by the battery or the wireless power reception device, power to operate the at least one IR-LED. In the scenario of FIG. 1A, 1B or 2, the step of providing power may be initiated by switching on switch 22 that electrically connects the battery 16 with the IR-LEDs 14. The switch 22 may be operated manually or by a wireless remote control.

The method further comprises limiting in step 74, by the electrical circuit, a current for at least one of the at least one IR-LED to not exceed 15 mA. The electrical circuit may comprise at least one resistor capable of limiting the current for at least one of the at least one IR-LED.

CLAUSES

I. A method of operating a tracker, wherein the tracker comprises a carrier and an electrical circuit disposed on the carrier, wherein the electrical circuit comprises at least one infrared light emitting diode, IR-LED, wherein the electrical circuit further comprises a battery or a wireless power reception device configured to receive power wirelessly, the method comprising
providing, by the battery or the wireless power reception device, power to operate the at least one IR-LED; and
limiting, by the electrical circuit, a current for at least one of the at least one IR-LED to not exceed 15 milliampere (mA).

The features described in relation to the exemplary embodiments shown in the drawings can be readily combined to result in different embodiments. It is apparent, therefore, that the present disclosure may be varied in many ways. Such variations are not to be regarded as a departure from the scope of the invention as defined by the claims appended hereto.

What is claimed is:

1. A tracker for a surgical navigation system, the tracker comprising:
a carrier; and
an electrical circuit disposed on the carrier, wherein the electrical circuit comprises:
at least three infrared light emitting diodes, IR-LEDs; and
only one battery configured to provide power to operate the at least three IR-LEDs, wherein the electrical circuit is configured to cause the at least three IR-LEDs to continuously and simultaneously emit infrared light for being sensed by a camera of the surgical navigation system by supplying a current through each of the at least three IR-LEDs that is limited to not exceed 15 milliampere (mA), wherein the battery is a button cell battery.

2. The tracker of claim 1, wherein the electrical circuit is configured to cause each of the at least three IR-LEDs to emit infrared light for being sensed by the surgical navigation system by supplying a current through each of the at least three IR-LEDs that is limited to not exceed 5 milliampere (mA).

3. The tracker of claim 1, wherein the tracker does not include a communication interface.

4. The tracker of claim 1, wherein the distance between any two of the at least three IR-LEDs is unique.

5. The tracker of claim 1, wherein the at least three IR-LEDs are arranged on a common plane and form a pattern lacking mirror symmetry and rotational symmetry.

6. The tracker according to claim 1, wherein the electrical circuit comprises at least one resistor configured to limit the current for the at least three IR-LEDs.

7. The tracker according to claim 6, wherein the at least three IR-LEDs are connected in parallel, and the at least one resistor comprises at least three resistors each electrically connected in series to a different one of the at least three IR-LEDs for limiting the current through the IR-LED.

8. The tracker according to claim 1, wherein the at least three IR-LEDs are disposed in a non-collinear arrangement, and a distance between two of the at least three IR-LEDs is less than 40 millimeters (mm).

9. The tracker of claim 8, wherein the at least three IR-LEDs are arranged on a common plane.

10. The tracker according to claim 1, further comprising an interface that is configured for coupling the tracker to a surgical instrument.

11. The tracker of claim 10, wherein a weight of the tracker is less than 100 grams.

12. The tracker according to claim 1, wherein the electrical circuit comprises at least one switch configured to electrically close and/or open at least one portion of the electrical circuit.

13. The tracker according to claim 12, wherein the tracker is a disposable item and the switch is operable exactly once to close the at least one portion of the electrical circuit.

14. The tracker of claim 13, wherein the battery is not removeable.

15. The tracker of claim 1, wherein the battery has a capacity of less than 400 milliamp hours, and the electrical circuit is configured to cause each of the at least three IR-LEDs to emit infrared light for being sensed by the surgical navigation system by supplying a current through each of the at least three IR-LEDs that is limited to not exceed 10 milliampere (mA).

16. The tracker of claim 15, wherein the tracker is configured for continuous and simultaneous operation of the at least three IR-LEDs for at least 5.5 hours.

17. The tracker of claim 16, further comprising an interface configured for coupling the tracker to a surgical instrument, wherein a weight of the tracker is less than 100 grams.

18. The tracker of claim 1, wherein the battery is not removable.

19. The tracker of claim 18, wherein tracker is not connectable to an external power source.

20. The tracker of claim 18, wherein the battery is not rechargeable.

* * * * *